United States Patent
Shan et al.

(10) Patent No.: US 8,133,736 B2
(45) Date of Patent: Mar. 13, 2012

(54) METHODS FOR DETECTING OR MONITORING CANCER USING LPE AS A MARKER

(75) Inventors: Lian Shan, Ithaca, NY (US); Lorelei D. Davis, East Lansing, MI (US); Rebecca Sutphen, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 12/775,958

(22) Filed: May 7, 2010

(65) Prior Publication Data

US 2011/0059543 A1    Mar. 10, 2011

Related U.S. Application Data

(63) Continuation of application No. PCT/US2008/012491, filed on Nov. 5, 2008.

(60) Provisional application No. 61/002,282, filed on Nov. 7, 2007, provisional application No. 61/002,989, filed on Nov. 14, 2007, provisional application No. 61/066,331, filed on Feb. 20, 2008.

(51) Int. Cl.
  *G01N 33/92* (2006.01)
  *G01N 33/48* (2006.01)

(52) U.S. Cl. ............... 436/64; 436/63; 436/71

(58) Field of Classification Search ........... 436/63, 436/64, 71, 104
  See application file for complete search history.

(56) References Cited

U.S. PATENT DOCUMENTS

| | | | |
|---|---|---|---|
| 6,248,553 B1 * | 6/2001 | Small et al. | 435/25 |
| 6,500,633 B1 | 12/2002 | Compton et al. | |
| 7,964,408 B1 * | 6/2011 | Sutphen | 436/64 |
| 2002/0039757 A1 * | 4/2002 | Small et al. | 435/25 |
| 2002/0123084 A1 | 9/2002 | Mills et al. | |
| 2002/0150955 A1 | 10/2002 | Mills et al. | |
| 2004/0137541 A1 | 7/2004 | Mills et al. | |
| 2007/0054268 A1 * | 3/2007 | Sutherland et al. | 435/6 |
| 2007/0196875 A1 | 8/2007 | Shan et al. | |
| 2008/0020472 A1 | 1/2008 | Shan et al. | |
| 2009/0127454 A1 * | 5/2009 | Ritchie et al. | 250/282 |
| 2010/0190662 A1 * | 7/2010 | Sutphen et al. | 506/18 |

FOREIGN PATENT DOCUMENTS

WO    2009061412 A1    5/2009

OTHER PUBLICATIONS

Zhang et al., Three Biomarkers Identified from Serum Proteomic Analysis for the Detection of Early Stage Ovarian Cancer, Cancer Research, 2004, vol. 64, pp. 5882-5890.
Noguchi et al., Identification of p2y9/GPR23 as a Novel G Protein-Coupled Receptor for Lysophosphatidic Acid, Structurally Distant from the Edg Family, The Journal of Biological Chemistry, 2003, vol. 278, No. 28, pp. 25600-25606.
International Search Report for PCT/US08/12491 dated Jan. 13, 2009.

\* cited by examiner

*Primary Examiner* — Maureen Wallenhorst
(74) *Attorney, Agent, or Firm* — Michele L. Lawson; Smith & Hopen, P.A.

(57) ABSTRACT

A method of detecting a cancer, such as ovarian cancer, in a test subject including (a) determining the amount of a lysophosphatidyl ethanolamine in a sample of a bodily fluid taken from the test subject, and (b) comparing the amount of the lysophosphatidyl ethanolamine in the sample of the bodily fluid taken from the test subject to a range of amounts of the lysophosphatidyl ethanolamine found in samples of the bodily fluid taken from a group of normal subjects of the same species as the test subject and lacking the cancer, such as ovarian cancer, whereby a change in the amount of the lysophosphatidyl ethanolamine in the sample of the bodily fluid from the test subject indicates the presence of the cancer, such as ovarian cancer.

7 Claims, 6 Drawing Sheets

METHODS FOR DETECTING OR MONITORING CANCER USING LPE AS A MARKER

CROSS REFERENCE TO RELATED APPLICATIONS

This application is a continuation of International Application No. PCT/US2008/012491 entitled, "Methods for Detecting or Monitoring Cancer Using LPE as a Marker", filed Nov. 5, 2008, the contents of which are herein incorporated by reference, which claims the benefit of priority to U.S. Provisional Patent Application 61/002,282, filed Nov. 7, 2007, the contents of which are herein incorporated by reference, U.S. Provisional Patent Application 61/002,989, filed Nov. 14, 2007, the contents of which are herein incorporated by reference, and U.S. Provisional Patent Application 61/066,331, filed Feb. 20, 2008, the contents of which are herein incorporated by reference.

STATEMENT OF GOVERNMENT INTEREST

This invention was made with Government support under Grant No. R01 CA106414 awarded by the National Institutes of Health (NIH). The Government has certain rights in the invention.

BACKGROUND OF THE INVENTION

1. Field of the Invention

Methods for detecting a cancer, such as ovarian cancer, are disclosed herein. Also discussed herein are methods for monitoring a cancer, such as ovarian cancer. More particularly, disclosed herein are methods for detecting ovarian cancer in a test subject by determining the amount of a lysophosphatidyl ethanolamine ("LPE") in a sample of a bodily fluid taken from the test subject. The methods discussed herein are particularly useful as a screening test for ovarian cancer.

2. Background Information

Ovarian cancer is one of the deadliest cancers for women, due to its high fatality rate. In the United States in 2007, it was estimated that 22,430 women would be diagnosed with ovarian cancer and 15,280 women would die of ovarian cancer. Unfortunately, heretofore, only 25% of ovarian cancer patients were diagnosed at stage I. Most of the patients were diagnosed at an advanced stage, stage III or IV, at which the 5-year survival rate decreases to 20 to 25% from 95% at stage I.

Presently, the most commonly used biomarker for diagnosing ovarian cancer is CA-125, a group of surface glycoproteins with uncertain biological function. Although CA-125 is elevated in 82% of women with advanced ovarian cancer, it has very limited clinical application for the detection of early stage disease, exhibiting a positive predictive value of less than 10%. The addition of physical examination by diagnostic ultrasound improves the positive predictive value to 20%, which is still too low to meet the requirement for cancer detection. Developing a clinical test to diagnose ovarian cancer with high sensitivity and specificity at the early stage has become the most urgent issue in battling this refractory disease.

Frequently, the detection of cancer depends upon the detection and inspection of a tumor mass, which has reached sufficient size to be detected by physical examination. The detection of molecular markers of carcinogenesis and tumor growth can solve many of the problems associated with the physical examination of tumors. Samples taken from the patient for screening by molecular techniques are typically blood or urine, and thus require minimally invasive techniques. Thus, they can be used on a regular basis to screen for cancers. In addition, because molecular markers may appear before the tumor reaches a detectable size; it is possible to detect cancers at very early stages in the progression of the disease.

Biomarkers identified from serum proteomic analysis for the detection of ovarian cancer are discussed in Z. Zhang et al., *Cancer Research*, 64, 5882-5890, Aug. 15, 2004.

Methods for detecting a cancer associated with elevated concentrations of lysophospholipids have been described in US 2002/0123084 and US 2002/0150955.

U.S. Pat. No. 6,500,633 discloses a method of detecting carcinomas by measuring the level of a glycerol compound, such as glycerol-3-phosphate, in a plasma, serum or urine specimen from a patient.

US 2007/0196875 (inventors: Lian Shan and Stanley L. Hazen) discloses a method for detecting ovarian cancer using plasmenyl-PA as a marker.

US 2008/0020472 (inventors: Lian Shan and Lorelei D. Davis) discloses a method for detecting ovarian cancer using plasmenyl-PE as a marker.

SUMMARY OF INVENTION

It is an object of the present invention to provide a non-invasive method for detecting a cancer, such as ovarian cancer, in a test subject.

It is another object of the present invention to utilize a molecular marker for the screening and diagnosis of a cancer, such as ovarian cancer.

It is a further object of the present invention to provide a non-invasive method to monitor the presence of a cancer, such as ovarian cancer, over time.

The above objects, as well as other objects, advantages and aims, are satisfied by the present invention.

The present invention concerns a method of detecting a cancer (for example, ovarian cancer) in a test subject comprising:
(a) determining the amount of a lysophosphatidyl ethanolamine in a sample of a bodily fluid taken from the test subject, and
(b) comparing the amount of the lysophosphatidyl ethanolamine in the sample of the bodily fluid taken from the test subject to a range of amounts found in samples of the bodily fluid taken from a group of normal subjects of the same species as the test subject and lacking the cancer (for example, if the bodily fluid taken from the test subject is serum, then the bodily fluid taken from each member of the group of normal subjects will also be serum), whereby a change in the amount (such as a lower amount) of the lysophosphatidyl ethanolamine in the sample of the bodily fluid taken from the test subject indicates the presence of the cancer (for example, ovarian cancer).

The present invention further concerns a method for monitoring a cancer (for example, ovarian cancer) in a test subject over time comprising:
(a) determining the amount of a lysophosphatidyl ethanolamine in a sample of a bodily fluid taken from the test subject at a first time,
(b) determining the amount of the lysophosphatidyl ethanolamine in a sample of the bodily fluid taken from the test subject at a second time (for example, if the bodily fluid in step (a) is serum, then the bodily fluid in step (b) will also be serum), which is later than the first time,
(c) comparing the amounts of the lysophosphatidyl ethanolamine in each of step (a) and step (b) to determine whether there has been an increase or a decrease in the amount of the lysophosphatidyl ethanolamine in a sample of the bodily fluid taken from the test subject at the later time relative to the amount of the lysophosphatidyl ethanolamine in the sample of the bodily fluid taken from the test subject at the first time, whereby a decrease from the amount of the lysophosphatidyl ethanolamine in the sample of the bodily fluid taken from the test subject at the later time indicates the presence of, or worsening of, the cancer (for example, ovarian cancer), or an increase from the amount of the lysophosphatidyl ethanolamine in the sample of the bodily fluid taken from the test subject at the later time indicates an absence, or improvement of, the cancer (for example, ovarian cancer).

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

Figure 1:
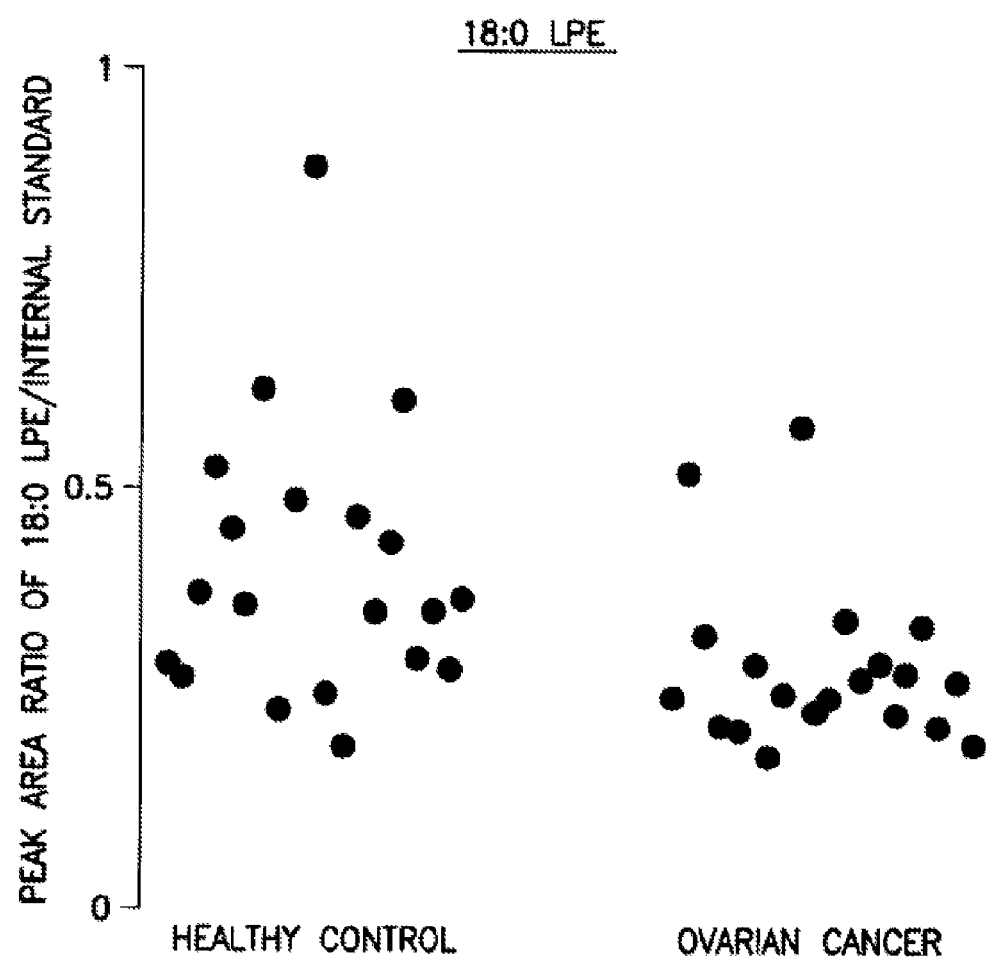
FIG. 1 is a graph showing the levels of 18:0 lysophosphatidyl ethanolamine ("18:0 LPE") in plasma samples from ovarian cancer patients and patients without ovarian cancer ("healthy controls").

In the following detailed description of the preferred embodiments, reference is made to the accompanying drawings, which form a part hereof, and within which are shown by way of illustration specific embodiments by which the invention, may be practiced. It is to be understood that other embodiments may be utilized and structural changes may be made without departing from the scope of the invention.

Applicants have discovered that the lipid lysophosphatidyl ethanolamine ("LPE") can be used in the methods disclosed herein for detecting a cancer, such as ovarian cancer, and monitoring a cancer, such as ovarian cancer, in a test subject.

Non-limiting examples of the lysophosphatidyl ethanolamine that can be used in the methods disclosed herein include the following: 18:0 LPE, 18:1 LPE, 18:2 LPE, 16:0 LPE, 22:6 LPE and 20:4 LPE.

The molecule weights, chemical names and structures for 16:0 LPE, 18:0 LPE, 18:1 LPE, 18:2 LPE, 20:4 LPE and 22:6 LPE are as follows:

16:0 LPE
mw 453.55

1-Palmitoyl-2-Hydroxy-sn-Glycero-3-Phosphoethanolamine

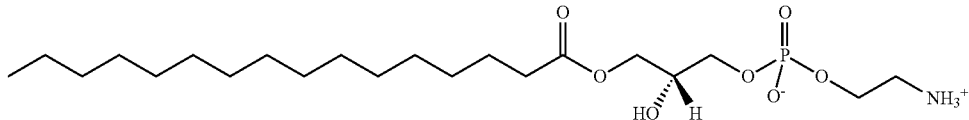

18:0 LPE
mw 481.61

1-Stearoyl-2-Hydroxy-sn-Glycero-3-Phosphoethanolamine

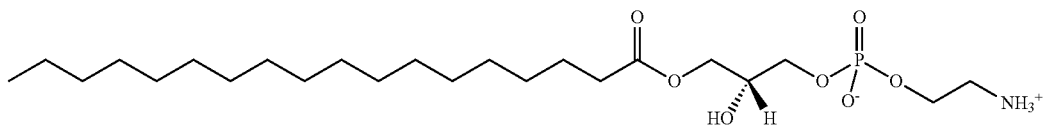

18:1 LPE
mw 479.59

1-Oleoyl-2-Hydroxy-sn-Glycero-3-Phosphoethanolamine

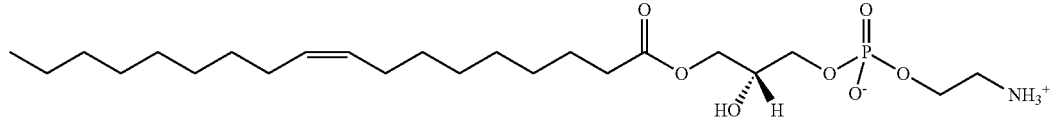

18:2 LPE
mw 477.58

1-linoleoyl-2-Hydroxy-sn-Glycero-3-Phosphoethanolamine

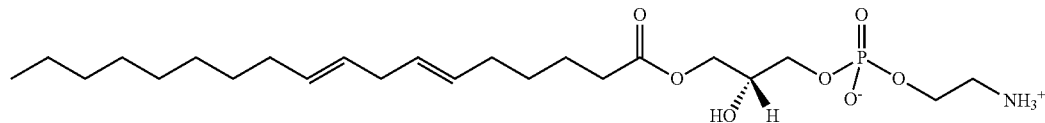

20:4 LPE
mw 501.59

1-Arachidonoyl-2-Hydroxy-sn-Glycero-3-Phosphoethanolamine

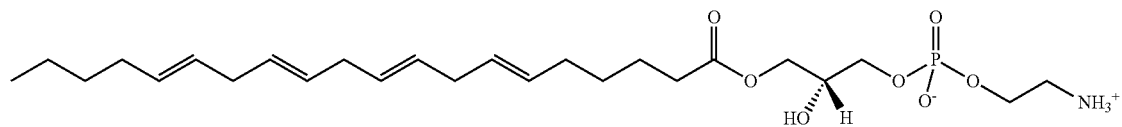

22:6 LPE
mw: 525.60

1-Docosahexaenoeyl-2-Hydroxy-sn-Glycero-3-Phosphoethanolamine

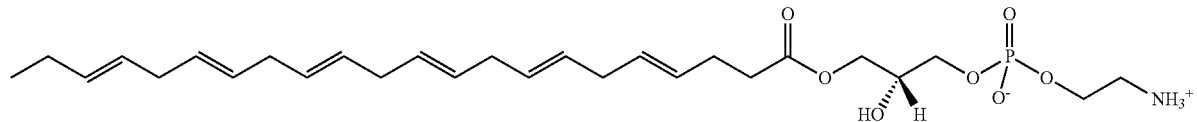

In an embodiment of the invention, an amount of a lysophosphatidyl ethanolamine ("LPE") found in a sample of a bodily fluid taken from a test subject is compared to the amount of the LPE found samples taken from normal subjects of the same species as the test subject lacking a cancer (for example, ovarian cancer) (e.g., if the test subject is a human, then the normal subject is a human who does not have the cancer (for example, ovarian cancer)). Thus, the amount of a LPE taken from a test subject, e.g., a female, is determined, and a range of amounts of LPE taken from normal females, e.g., lacking ovarian cancer, is obtained. A lower amount of the LPE found in the sample of the bodily fluid taken from the test subject when compared to a range of amounts of the LPE in samples of the bodily fluid taken from a group of normal subjects of the same species as the test subject and lacking the cancer (for example, ovarian cancer), indicates the presence of the cancer (for example, ovarian cancer).

The amount of the LPE detected in the sample taken from a test subject may be measured by first extracting lipids as described in detail infra. The amount of the LPE is then quantified using standard procedures, such as mass spectroscopy, gas chromatography, HPLC, NMR or other approaches.

In addition to the direct measurement of the LPE by extraction, antibodies, such as monoclonal antibodies reactive with the LPE can be used in an assay to detect the amount of the LPE. For example, anti-LPE antibodies may be labeled using standard procedures and used in assays including radioimmunoassay (RIA), both solid and liquid phase, fluorescence-linked assays or enzyme-linked immunosorbent assays (ELISA), wherein the antibody is used to detect the presence and amount of the LPE.

The test subject can be a eukaryotic organism, preferably a vertebrate, including, but not limited to, a mammal, a bird, a fish, an amphibian or a reptile. Preferably, the subject is a mammal, most preferably a human. The bodily fluid includes, but is not limited to, plasma, serum, urine, saliva, ascites, cerebral spinal fluid or pleural fluid. Preferably, the bodily fluid is plasma or a serum which is obtained from a whole blood specimen from the test subject.

The methods disclosed herein can be used to detect, screen or monitor for a broad range of cancers at an early stage. Such cancers include gynecological cancers, including ovarian cancer, breast cancer, cervical cancer, uterine cancer, endometrial cancer, peritoneal cancer, fallopian tube cancer and vulva cancer. Other cancers that can be detected, screened or monitored according to the methods disclosed herein include, but are not limited to, testicular cancer, colon cancer, lung cancer, prostate cancer, bladder cancer, kidney cancer, thyroid cancer, stomach cancer, pancreatic cancer, brain cancer, liver cancer, ureter cancer, esophageal cancer and larynx cancer. The methods disclosed herein are preferably directed to detecting ovarian cancer.

The methods disclosed herein are non-invasive and require only a bodily fluid specimen, such as a blood specimen from the test subject (patient). Thus, such methods are particularly useful for screening patients who have not been previously diagnosed as having ovarian cancer. Such patients include women at elevated risk by virtue of a family history of the disease, premenopausal women with anovulatory cycles and postmenopausal women. The methods disclosed herein include a screening test for identifying within a risk population, a subject population with a greater propensity for developing ovarian cancer.

The methods disclosed herein can provide a number of benefits. First, the methods provide a rapid and economical screen for large numbers of subjects to promote early diagnosis of ovarian cancer, which can result in improved quality of life and better survival rates for patients.

Using the methods disclosed herein for prognosis, the medical professional can determine whether a subject having ovarian cancer in the early stages requires therapy or does not require therapy. This could also identify subjects who may not benefit from a particular form of therapy, e.g., surgery, chemotherapy, radiation or biological therapies. Such information could result in an improved therapy design for obtaining better responses to therapy.

The methods disclosed herein can also be used to identify patients for whom therapy should be altered from one therapeutic agent to another. This could obviate the need for "second look" invasive procedures to determine the patient's response to the therapy and facilitate decisions as to whether the particular type of therapy should be continued, terminated or altered.

Because cancers may recur in a significant number of patients with advanced cancers, early detection and continued monitoring over time using the methods disclosed herein can identify early occult (i.e., "hidden") recurrences prior to symptoms presenting themselves.

In addition, methods disclosed herein will facilitate distinguishing benign from malignant tumors. Masses in the ovary can be initially detected using procedures such as ultrasound or by physical examination. Thereafter, the methods disclosed herein can be used to diagnose the presence of a cancer (for example, ovarian cancer). This could obviate the need for surgical intervention, and/or identify subjects for whom continued monitoring is appropriate, resulting in improved early detection and survival for ovarian cancer patients.

EXAMPLES

The present invention will now be described in the context of the following non-limiting examples:

Example 1

Quantitative Determination of LPE Levels in Human Plasma (a) Extraction of LPE from Human Plasma LPE in plasma was extracted using a modified Bligh-Dyer method, which follows the following procedure: First mix 200 pmol 14:0 LPE with 200 µl plasma. The mixture was vortexed and 2 ml 2:1 (v:v) methanol-chloroform was added. The mixture was vortexed again and kept at room temperature for 10 minutes. Then it was centrifuged at 4000 rpm at 10° C. for 10 minutes. The top liquid layer was transferred into another tube and dried under nitrogen. The dried pellet was dissolved in 200 µl 100 mM ammonium acetate in methanol and centrifuged at 9000 rpm for 5 minutes. 50 µl of the supernatant was injected and analyzed by LC/ESI/MS/MS.

(b) LC/ESI/MS/MS Analysis of LPE

LC/ESI/MS/MS analysis of LPE species was performed using a Quattro Micro mass spectrometer (Micromass, Altrincham, U.K.) equipped with an electrospray ionization (ESI) probe and interfaced with a Shimadzu SCL-10Avp HPLC system (Shimadzu, Tokyo, Japan). Lipids were separated with a Betabasic-18 column (20×2.1 mm, 5 µm, Thermo Electron, Waltham, Mass.), protected by a Betabasic 18 precolumn (10×2.1 mm, 5 µm, Thermo Electron, Waltham, Mass.). 1 mM ammonium acetate aqueous solution was used as mobile phase A and 1 mM ammonium acetate in methanol was used as mobile phase B. The flow rate was 200 µl/minute. The gradient used was as follows: the column was first equilibrated with 50% B (50% A), followed by a linear change from 50% B (50% A) to 100% B (0% A) in the first 4 minutes. The gradient was kept at 100% B in the following 8 minutes. In the following 4 minutes, the gradient was changed back to 50% B (50% A) to re-equilibrate the column. Mass spectrometric analyses were performed online using electrospray ionization tandem mass spectrometry in the negative multiple reaction monitoring (MRM) mode. The MS parameters are: capillary voltage, 3.0 KV; cone voltage, 35 V; source temperature, 100° C.; desolvation temperature, 350° C.; flow rate of desolvation gas, 500 L/hr; flow rate of cone gas, 50 L/hr; mass resolution of both parent and daughter ions, 15.0; multiplier, 650. The MRM transitions used to detect LPE were the mass to charge ratio (m/z) for their molecular anion $M^-$ and their corresponding daughter ion (collision energy 25 eV).

(c) Levels of LPE

The levels of 16:0 LPE, 18:2 LPE, 18:1 LPE, 18:0 LPE, 20:4 LPE and 22.6 LPE were determined in a negative MRM mode. The MRM transitions used to detect them were the mass to charge ratio (m/z) for their molecular anion $M^-$ and their corresponding daughter ion (collision energy 25 eV).

Example 2

Data Analysis

Figure 2:
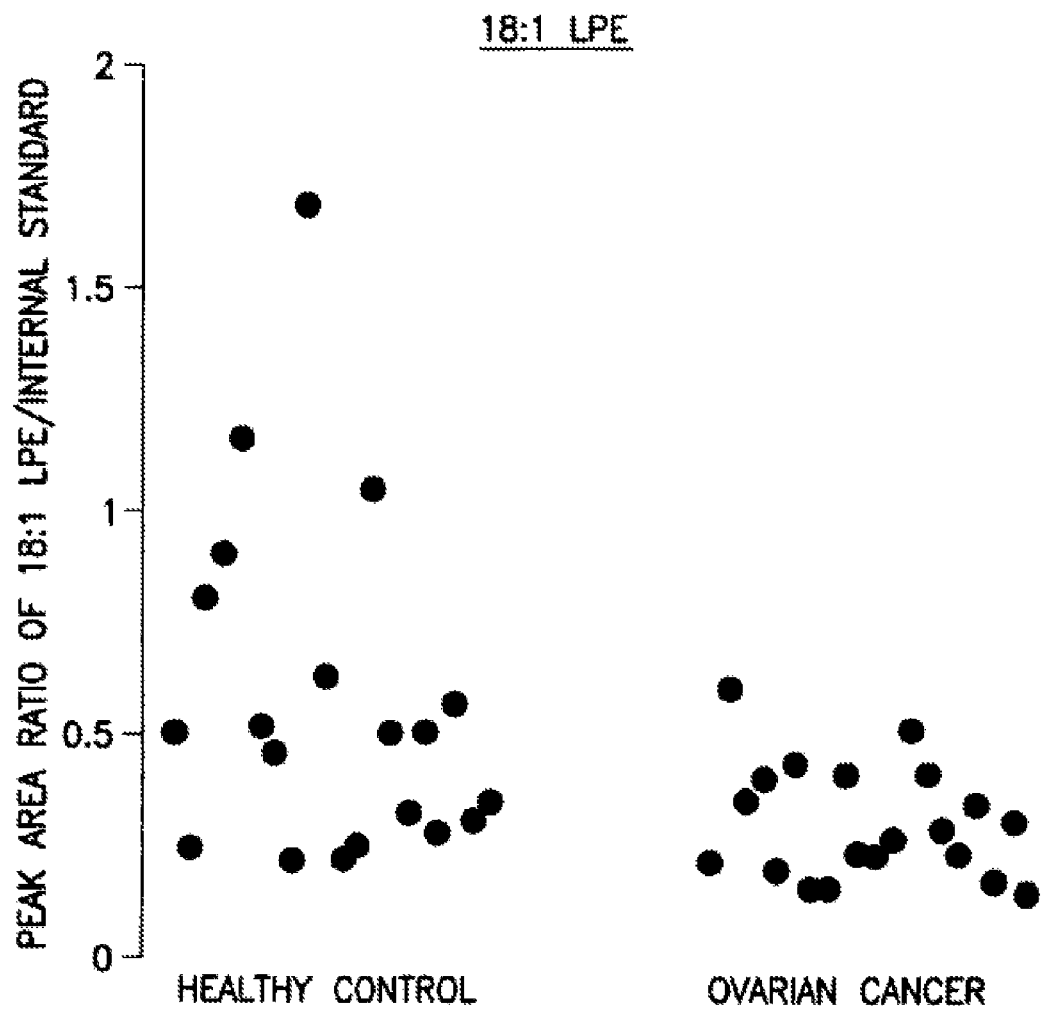
FIG. 2 is a graph showing the levels of 18:1 lysophosphatidyl ethanolamine ("18:1 LPE") in plasma samples from ovarian cancer patients and patients without ovarian cancer ("healthy controls").
Figure 3:
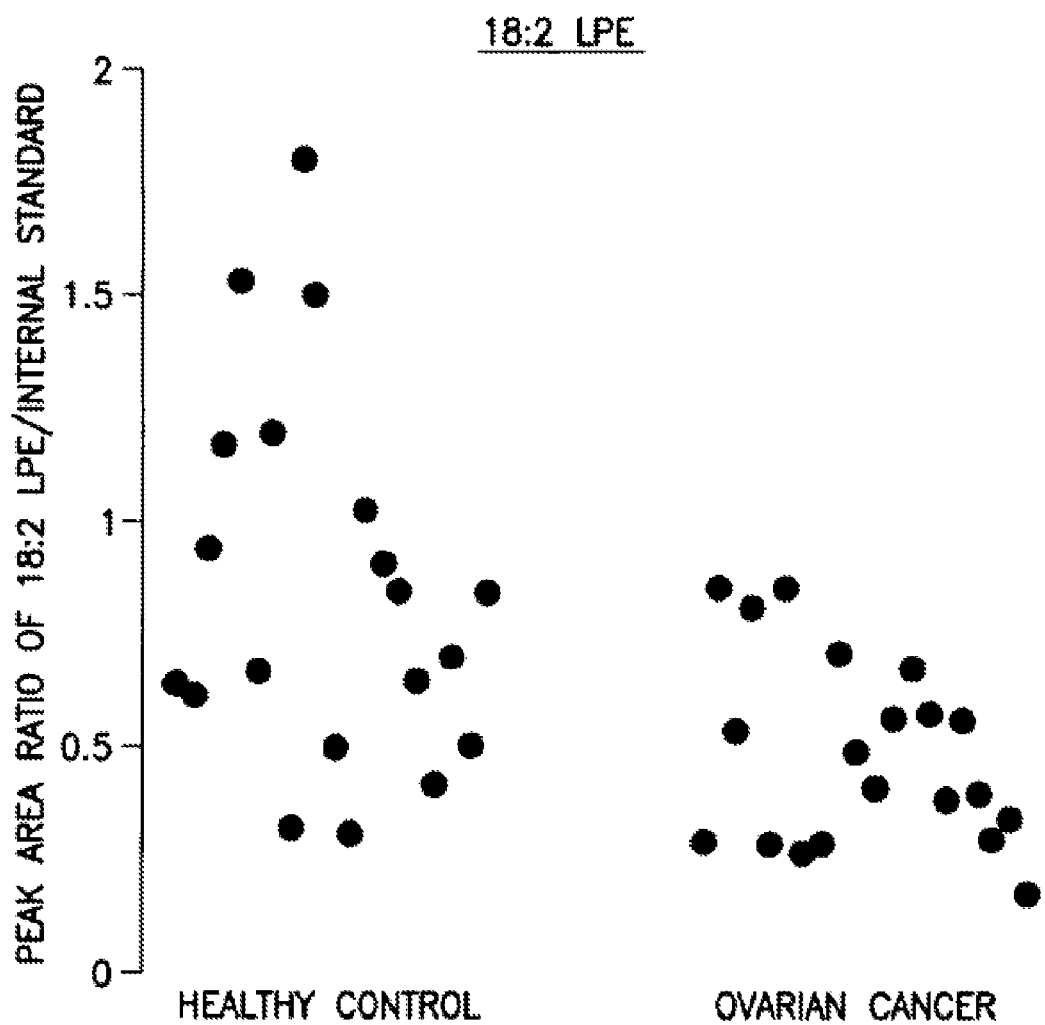
FIG. 3 is a graph showing the levels of 18:2 lysophosphatidyl ethanolamine ("18:2 LPE") in plasma samples from ovarian cancer patients and patients without ovarian cancer ("healthy controls").
Figure 4:
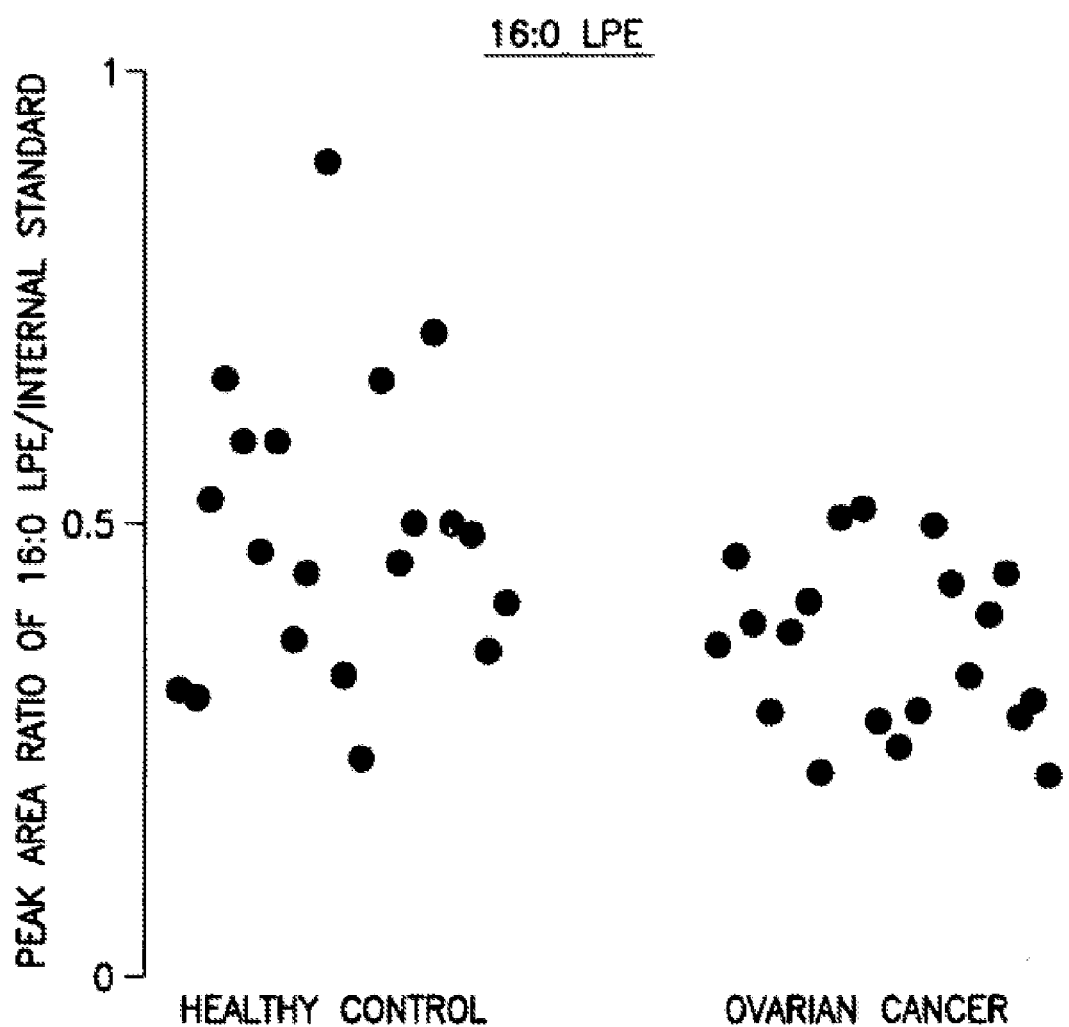
FIG. 4 is a graph showing the levels of 16:0 lysophosphatidyl ethanolamine ("16:0 LPE") in plasma samples from ovarian cancer patients and patients without ovarian cancer ("healthy controls").
Figure 5:
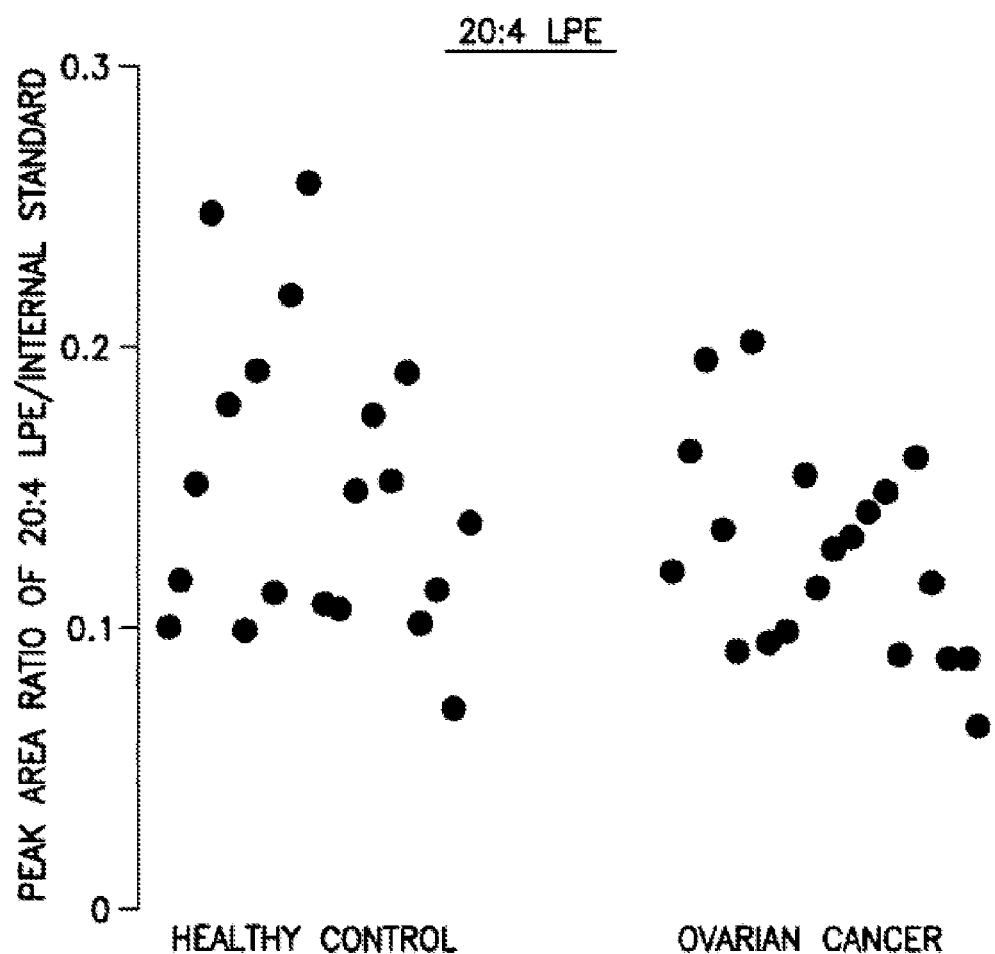
FIG. 5 is a graph showing the levels of 20:4 lysophosphatidyl ethanolamine ("20:4 LPE") in plasma samples from ovarian cancer patients and patients without ovarian cancer ("healthy controls").
Figure 6:
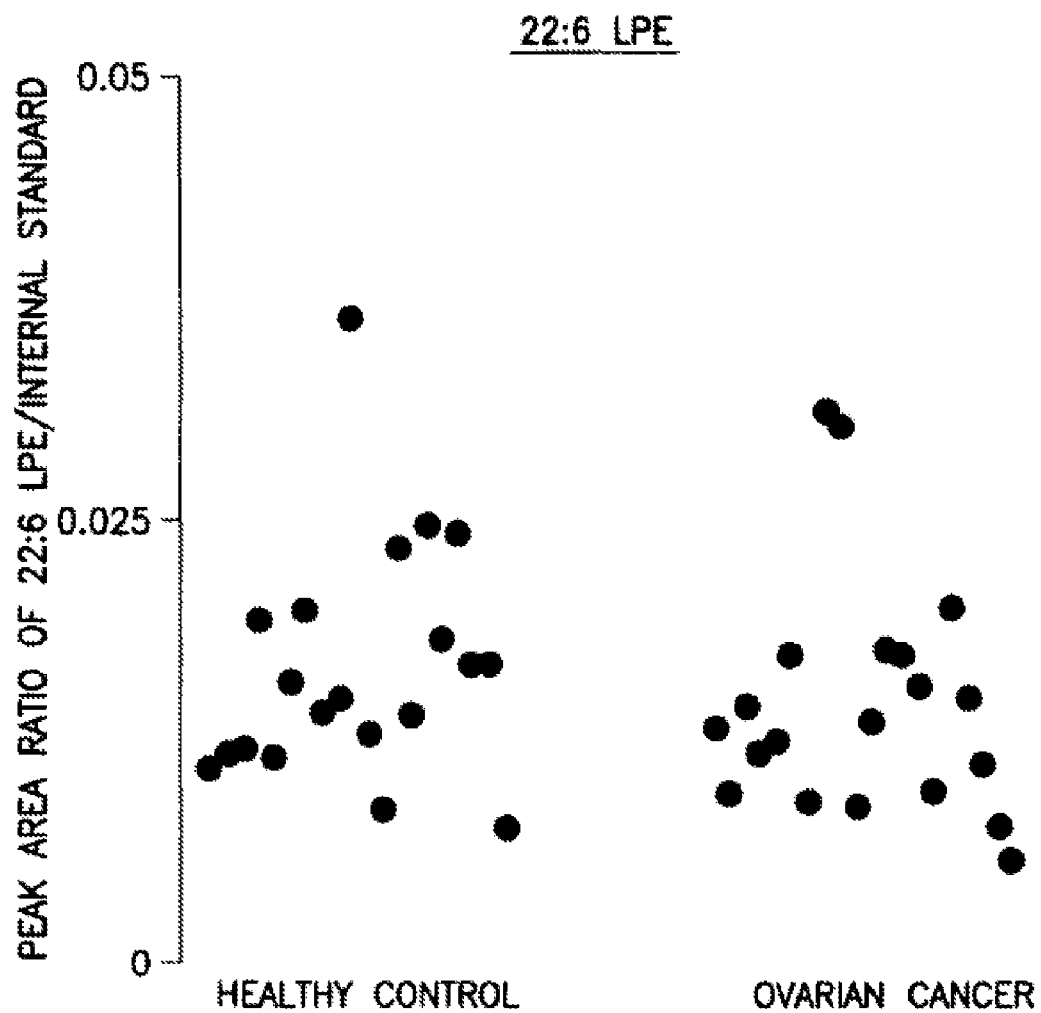
FIG. 6 is a graph showing the levels of 22:6 lysophosphatidyl ethanolamine ("22:6 LPE") in plasma samples from ovarian cancer patients and patients without ovarian cancer ("healthy controls").

Data analysis was done using the student t-test and the peak area ratio of analyte to internal standard was determined. The results are shown in FIG. 1 to FIG. 6.

Forty (40) plasma samples were collected. Among them were twenty (20) stage III ovarian cancer patients and twenty (20) healthy controls. The LPE data are expressed as peak area ratio of the LPE and its internal standard, 14:0 LPE. The results are shown in Table 1 below and in FIGS. 1 to 6. Table 1 describes the LPE, their corresponding standard deviation, and the p value of ovarian cancer patients related to healthy controls.

TABLE 1

Levels of 16:0 LPE, 18:2 LPE, 18:1 LPE, 18:0 LPE, 20:4 LPE, 22:6

| | Ovarian Cancer | | Healthy control | | |
| --- | --- | --- | --- | --- | --- |
| | LPE level | Standard Deviation | LPE level | Standard Deviation | p value |
| 16:0 LPE | 0.359 | 0.095 | 0.490 | 0.160 | <0.01 |
| 18:2 LPE | 0.472 | 0.212 | 0.853 | 0.426 | <0.01 |
| 18:1 LPE | 0.285 | 0.128 | 0.568 | 0.379 | <0.01 |
| 18:0 LPE | 0.382 | 0.100 | 0.403 | 0.162 | <0.01 |
| 20:4 LPE | 0.123 | 0.037 | 0.147 | 0.052 | 0.10 |
| 22:6 LPE | 0.0138 | 0.0067 | 0.0164 | 0.0068 | 0.23 |

It will be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method of detecting ovarian cancer in a test subject comprising:
   (a) determining the amount of a lysophosphatidyl ethanolamine in a sample of a bodily fluid taken from the test subject; and
   (b) comparing the amount of the lysophosphatidyl ethanolamine in the sample of the bodily fluid from the test subject to a range of amounts of the lysophosphatidyl ethanolamine found in samples of the bodily fluid taken from a group of normal subjects of the same species as the test subject and lacking ovarian cancer;
   whereby a decrease of a mass spectrometer peak area ratio of lysophosphatidyl ethanolamine to internal standard of at least 0.021 in the amount of the lysophosphatidyl ethanolamine in the sample of the bodily fluid from the test subject as compared to the amount of the lysophosphatidyl ethanolamine in the samples of the bodily fluid taken from the group of normal subjects lacking ovarian cancer indicates the presence of ovarian cancer in the test subject.

2. The method of claim 1, wherein the test subject is a human.

3. The method of claim 1, wherein the bodily fluid is plasma.

4. The method of claim 1, wherein the lysophosphatidyl ethanolamine is selected from the group consisting of 18:0 LPE, 18:1 LPE, 18:2 LPE, and 16:0 LPE.

5. A method for monitoring ovarian cancer in a test subject over time comprising:
   (a) determining the amount of a lysophosphatidyl ethanolamine in a sample of a bodily fluid taken from a test subject at a first time;
   (b) determining the amount of the lysophosphatidyl ethanolamine in a sample of the bodily fluid taken from the test subject at a second time, which is later than the first time;
   (c) comparing the amounts of the lysophosphatidyl ethanolamine in each of step (a) and step (b) to determine whether there has been an increase or a decrease in the amount of the lysophosphatidyl ethanolamine in the sample of the bodily fluid taken from the test subject at the later time relative to the amount of the lysophosphatidyl ethanolamine in the sample of the bodily fluid taken from the test subject at the first time;
   whereby a decrease of a mass spectrometer peak area ratio of lysophosphatidyl ethanolamine to internal standard of at least 0.021 from the amount of the lysophosphatidyl ethanolamine in the sample of the bodily fluid taken from the test subject at the later time as compared to the amount of lysophosphatidyl ethanolamine in the sample of the bodily fluid taken from the test subject at the first time indicates the presence of or worsening of ovarian cancer in the test subject, or an increase of a mass spectrometer peak area ratio of lysophosphatidyl ethanolamine to internal standard from the amount of the lysophosphatidyl ethanolamine in the sample of the bodily fluid taken from the test subject at the later time as compared to the first time indicates an improvement of ovarian cancer in the test subject.

6. The method of claim 5, wherein the test subject is a human.

7. The method of claim 5, wherein the lysophosphatidyl ethanolamine is selected from the group consisting of 18:0 LPE, 18:1 LPE, 18:2 LPE, and 16:0 LPE.

* * * * *